(12) United States Patent
Ozaki

(10) Patent No.: US 9,724,995 B2
(45) Date of Patent: Aug. 8, 2017

(54) DIAGNOSTIC METHOD FOR MOTOR

(75) Inventor: Takayoshi Ozaki, Iwata (JP)

(73) Assignee: NTN CORPORATION, Osaka (JP)

( * ) Notice: Subject to any disclaimer, the term of this patent is extended or adjusted under 35 U.S.C. 154(b) by 20 days.

(21) Appl. No.: 14/003,943

(22) PCT Filed: Mar. 5, 2012

(86) PCT No.: PCT/JP2012/055535
§ 371 (c)(1),
(2), (4) Date: Sep. 9, 2013

(87) PCT Pub. No.: WO2012/121201
PCT Pub. Date: Sep. 13, 2012

(65) Prior Publication Data
US 2013/0342150 A1    Dec. 26, 2013

(30) Foreign Application Priority Data
Mar. 9, 2011    (JP) .................................. 2011-051383

(51) Int. Cl.
*H02P 1/04*        (2006.01)
*B60L 3/04*        (2006.01)
(Continued)

(52) U.S. Cl.
CPC .............. *B60L 3/04* (2013.01); *B60K 7/0007* (2013.01); *B60L 3/0061* (2013.01);
(Continued)

(58) Field of Classification Search
CPC ........ G01F 23/00; G01F 1/7086; G01F 25/00; G01F 1/007; G01F 1/64; G01F 1/661; G01F 1/696
(Continued)

(56) References Cited

U.S. PATENT DOCUMENTS 5,377,531 A * 1/1995 Gomm ......................... 73/53.05
7,395,810 B2 * 7/2008 Miyashita et al. ....... 123/406.13
(Continued)

FOREIGN PATENT DOCUMENTS

CN    101029585    9/2007
CN    101720288    6/2010
(Continued)

OTHER PUBLICATIONS

Harley-Davisdon Company, LCD Oil Temperature/Level Dipstick, Oct. 31, 2007, pp. 1-3.*
(Continued)

*Primary Examiner* — Bickey Dhakal

(57) ABSTRACT

In a diagnostic device and a diagnostic method for a motor unit of an electric vehicle, an oil degradation/others detection unit is provided which is configured to detect at least any one detection item of a contamination degree, a degradation degree, and an oil amount of an oil used for cooling a motor unit or a reduction gear unit during a non-traveling period when the vehicle is powered on. An abnormalities-time control unit is provided which is configured to send notice of abnormalities of an oil supply system or not permit start of rotation of the motor unit when a detection value detected by the oil degradation/others detection unit is out of a setting range.

14 Claims, 6 Drawing Sheets

A: TIRE ROT FREQ    D: DEC CMD        G: CUR CMD
B: ACC CMD          E: IWM SYS INFO   H: MOTOR CUR
C: CORNERING CMD    F: ACC/DEC CMD    I: ROTOR ANG

(51) Int. Cl.
| | |
|---|---|
| *B60L 3/00* | (2006.01) |
| *B60L 15/20* | (2006.01) |
| *B60W 50/02* | (2012.01) |
| *B60K 7/00* | (2006.01) |
| *B60L 11/18* | (2006.01) |
| *F16H 57/04* | (2010.01) |
| *G01N 33/28* | (2006.01) |
| *F16H 1/32* | (2006.01) |

(52) U.S. Cl.
CPC ....... *B60L 11/1818* (2013.01); *B60L 15/2036* (2013.01); *B60L 15/2072* (2013.01); *B60W 50/0205* (2013.01); *F16H 57/0405* (2013.01); *F16H 57/0476* (2013.01); *G01N 33/2888* (2013.01); *B60K 2007/0092* (2013.01); *B60L 2240/36* (2013.01); *B60L 2240/425* (2013.01); *B60L 2240/427* (2013.01); *B60L 2240/429* (2013.01); *B60L 2240/80* (2013.01); *B60L 2250/10* (2013.01); *B60L 2250/16* (2013.01); *B60W 2050/022* (2013.01); *F16H 1/32* (2013.01); *Y02T 10/645* (2013.01); *Y02T 10/7005* (2013.01); *Y02T 10/7072* (2013.01); *Y02T 10/72* (2013.01); *Y02T 10/7275* (2013.01); *Y02T 90/14* (2013.01)

(58) Field of Classification Search
USPC .......................................... 318/473, 482, 483
See application file for complete search history.

(56) References Cited

U.S. PATENT DOCUMENTS

| | | | | |
|---|---|---|---|---|
| 8,224,600 | B2* | 7/2012 | Akiyama et al. ............... | 702/65 |
| 8,290,674 | B2 | 10/2012 | Miyazaki et al. | |
| 8,355,880 | B2* | 1/2013 | Halalay et al. ................. | 702/50 |
| 8,521,451 | B2* | 8/2013 | Kong et al. ..................... | 702/50 |
| 2001/0035676 | A1* | 11/2001 | Miyazaki .............. | B60T 8/1708 303/113.1 |
| 2007/0151806 | A1* | 7/2007 | Boyle ................ | G01N 33/2888 184/6.21 |
| 2007/0204833 | A1 | 9/2007 | Miyashita et al. | |
| 2009/0216471 | A1 | 8/2009 | Akiyama et al. | |
| 2010/0198476 | A1 | 8/2010 | Miyazaki et al. | |
| 2010/0321030 | A1* | 12/2010 | Gale et al. .................... | 324/537 |

FOREIGN PATENT DOCUMENTS

| | | | |
|---|---|---|---|
| EP | 0121739 | A2 | 10/1984 |
| EP | 99/28149 | | 6/1999 |
| EP | 1217261 | A2 | 6/2002 |
| JP | 2006-248417 | | 9/2006 |
| JP | 2006-299827 | | 11/2006 |
| JP | 2007-231847 | | 9/2007 |
| JP | 2008-168790 | | 7/2008 |
| JP | 2009-40162 | | 2/2009 |
| JP | 2009-198341 | | 9/2009 |
| JP | 2009215888 | A * | 9/2009 |
| WO | 02/24482 | A1 | 3/2002 |

OTHER PUBLICATIONS

PCT International Preliminary Report on Patentability mailed Sep. 19, 2013 in corresponding International Application No. PCT/JP2012/055535.

Japanese Office Action issued Jul. 22, 2014 in corresponding Japanese Patent Application No. 2011-051383.

International Search report mailed May 1, 2012 in corresponding International Application No. PCT/JP2012/055535.

Chinese Office Action issued May 6, 2015 in corresponding Chinese Patent Application No. 201280011859.1.

Extended European Search Report mailed Nov. 11, 2015 in related European Application No. 12755127.3.

Rockwell Automation, "Installation and Parts Replacement Manual for Dodge® TORQUE-ARM™ TXT Double Reduction Taper Bushed and Straight Bore Speed Reducers", Aug. 6, 2008, XP55224924, Retrieved from the Internet: URL:https:jjwww.applied.com/staticjcatalog/pdfsjtorqarm txt hxt.pdf, pp. 1-24.

\* cited by examiner

OUTBOARD SIDE ← 4 | 7 | 6 → INBOARD SIDE

DIAGNOSTIC METHOD FOR MOTOR

CROSS REFERENCE TO THE RELATED APPLICATION

This application is a U.S. national stage application of PCT/JP2012/055535, filed Mar. 5, 2012, and is based on and claims foreign priority benefit of Japanese patent application No. 2011-051383, filed Mar. 9, 2011, in the Japanese Intellectual Property Office, the entire disclosure of both of which are herein incorporated by reference as a part of this application.

BACKGROUND OF THE INVENTION

Field of the Invention

The present invention relates to a diagnostic device and a diagnostic method for a motor unit of an electric vehicle, and relates to a self-diagnosis function of an oil supply system that supplies an oil used for lubricating a reduction gear unit or cooling the motor unit.

Description of Related Art

An electric vehicle may experience a malfunction of a motor unit for driving the vehicle or a malfunction of a controller that controls the motor unit. This can significantly affect the travel performance or travel safety. In particular, in the case where an in-wheel motor drive apparatus is used in an electric vehicle, rapid rotation of a wheel bearing unit, a reduction gear unit, and a motor unit, which are components of the apparatus, is involved as a result of size reduction of the apparatus. Thus, reliability of these components is an urgent concern for the in-wheel motor drive apparatus. Hitherto, an in-wheel motor drive apparatus has been proposed in which, in order to ensure the reliability, during traveling of a vehicle, the temperature of components such as a wheel bearing unit, a reduction gear unit, and a motor unit is measured and monitored for overload with features to limit a drive current in the motor unit or to reduce a rotational frequency of the motor unit according to the temperature measurements (e.g., see the Patent Document 1 listed below).

[Prior Art Literature]

[Patent Document 1] JP Laid-open Patent Publication No. 2008-168790

In an in-wheel motor type electric vehicle, a motor unit having high responsibility is independently mounted to each wheel. In particular, in the case where drive torque of each motor unit which is a drive source of the electric vehicle is transmitted to the corresponding wheel via a reduction gear unit having a high reduction gear ratio, torque of each motor unit caused by destabilization of motor control is increased and transmitted to the corresponding wheel. Thus, at a time of a malfunction of the motor unit or the reduction gear unit, it is necessary to take measures corresponding to the situation in order to keep a stable vehicle attitude.

In each motor unit, a rotor and a stator are cooled directly by an oil, and the reduction gear unit is lubricated and cooled by this oil. In order to prevent a malfunction of the reduction gear unit, it has been necessary to grasp the contamination state, the degradation state, or the amount of the oil and to issue a warning when it is out of a specified value, thereby prompting maintenance of the vehicle. However, air is mixed into the oil during rotation of the reduction gear unit, and thus it is difficult to measure the degradation state or the like of the oil.

As described above, in the in-wheel motor drive apparatus, during traveling of the vehicle, the temperature of the motor unit is measured and monitored for overload, and driving of the motor unit is restricted. In this case as well, during traveling of the vehicle, the reduction gear unit rotates, the oil bubbles, and air is mixed into the oil. Thus, it is difficult to measure the degradation state or the like of the oil.

SUMMARY OF THE INVENTION

An object of the present invention is to provide a diagnostic device and a diagnostic method for a motor unit of an electric vehicle, which allow a degradation state or the like of an oil to be easily measured, allow a malfunction of a reduction gear unit to be prevented or allow a cooling effect on a motor unit to be kept high, and allow maintenance of a vehicle to be prompted. The general aspects of the present invention will now be described using the reference signs in the figures showing embodiments of the present invention.

A diagnostic device according to the present invention is a diagnostic device for a motor unit 6 of an electric vehicle including the motor unit 6 configured to drive a wheel 2; a reduction gear unit 7 configured to produce rotation with a speed that is reduced with respect to that of rotation of the motor unit 6; and an oil supply system configured to supply an oil that is used for any one or both of lubrication of the reduction gear unit 7 and cooling of the motor unit 6. The diagnostic device includes: an oil degradation/others detection unit 37 configured to detect at least any one detection item of a contamination degree, a degradation degree, and an oil amount of the oil during a non-traveling period when the vehicle is powered on; and an abnormalities-time control unit 40 configured to send notice of abnormalities of the oil supply system or not permit start of rotation of the motor unit 6 when a detection value detected by the oil degradation/others detection unit 37 is out of a setting range.

The "non-traveling period when the vehicle is powered on" refers to a time when a control unit, such as an ECU 21, configured to control the entirety of the vehicle is powered on with a key or the like but power is not supplied to the motor unit 6, or a time when power is not supplied to the motor unit 6 for stopping traveling but the unit configured to control the entirety of the vehicle is kept powered on, such as a time of start-up from a time when a driver gets in the vehicle to a time when traveling is started.

According to this aspect, during the non-traveling period when the vehicle is powered on, the oil degradation/others detection unit 37 detects at least any one detection item of the contamination degree, the degradation degree, and the oil amount of the oil. When a start-up unit such as a key or a start button is at a position of "accessory power" which is prior to power supply to the motor unit 6, it is determined that it is during the non-traveling period when the vehicle is powered on. In addition, when the start-up unit is at a position of "ON" and when it is determined that power supply to the motor unit 6 is not performed, based on a motor current from a current sensor 35, information indicating a rotational frequency of a tire produced from a rotation sensor 24, information produced from various sensors that may be mounted to the vehicle, or the like, it is determined that it is during the non-traveling period when the vehicle is powered on.

During such a non-traveling period when the vehicle is powered on, it is possible to reduce bubbling of the oil by stopping rotation of the reduction gear unit 7, and the degradation state or the like of the oil can be easily and accurately measured. When the measured detection value is out of the setting range, the abnormalities-time control unit 40 sends notice of abnormalities of the oil supply system or performs control such that start of rotation of the motor unit 6 is not permitted. As described above, for example, as one of checking items in checking abnormalities of the entire vehicle at a stage prior to traveling of the vehicle, etc., or at a time of a stop after start of traveling, abnormalities of the oil supply system can be diagnosed. When notice of abnormalities of the oil supply system are sent or when start of rotation of the motor unit 6 is not permitted, the oil supply system and the like are to be repaired, or rescue of the vehicle can be requested.

The oil degradation/others detection unit 37 may detect the detection item of the oil after elapse of a time period or longer during which time period air mixed in the oil is being released out of the oil. For example, immediately after a stop after start of traveling, it is in a state where air is mixed in the oil. Thus, the oil degradation/others detection unit 37 detects the detection item of the oil after elapse of the time period or longer during which time period the air mixed in the oil is being released out of the oil. The time period is set based on an experiment or the like.

The oil supply system may include a tank 46 configured to store the oil therein, and the oil degradation/others detection unit 37 may include a detector provided within the tank 46. The tank 46 may be provided so as to be integrated with the motor unit 6 and the reduction gear unit 7, or may be provided so as to be separate from the motor unit 6 and the reduction gear unit 7. Since the detector of the oil degradation/others detection unit 37 is provided within the tank 46, the detector can be easily installed. Since the oil can be stored within the tank 46, abnormalities of the oil supply system can be stably diagnosed in any of a time of start-up and a time of stopping traveling.

The oil degradation/others detection unit 37 may include a contamination degree detector 37a configured to detect the contamination degree of the oil, and the contamination degree detector 37a may include a measurer configured to measure a light transmittance in the oil. The light transmittance in the oil is proportional to the contamination degree of the oil. The relationship between them is stored in a table or the like. Light emitted from a light source 43 is guided into the oil by an optical fiber 44, and the light transmittance in the oil is measured by, for example, a light receiver 45 which is the measurer. The contamination degree of the oil can be easily detected by checking the measured light transmittance against the table or the like.

The oil degradation/others detection unit 37 may include a degradation degree detector 37b configured to detect the degradation degree of the oil, and the degradation degree detector 37b may include two electrodes 49, 49 provided within the oil so as to be spaced apart from each other, a detection power source 50 configured to apply an AC voltage between these electrodes 49, 49, and a dielectric constant calculator 51 configured to obtain a dielectric constant of the oil when the AC voltage is applied between the two electrodes 49, 49 by the detection power source 50. The AC voltage is applied between the two electrodes 49, 49 by the detection power source 50. Since the interval between the two electrodes 49, 49 and the surface areas of the flat surfaces of the electrodes 49, 49 are known, the dielectric constant calculator 51 can obtain the dielectric constant of the oil from the capacitance of the oil present between the electrodes 49, 49, the resistance between the electrodes 49, 49, and the like. The degradation degree of the oil can be detected based on the dielectric constant of the oil.

The oil degradation/others detection unit 37 may include an oil temperature detector 47 configured to detect a temperature of the oil, and a viscosity detector 48 configured to obtain a viscosity of the oil based on the temperature of the oil detected by the oil temperature detector 47. When the viscosity of the oil obtained by the viscosity detector 48 is out of the setting range, degradation or contamination of the oil is considered as having proceeded, and it is inferred that the oil supply system is abnormal. A determining section 39 configured to determine whether a value obtained by processing, through a low-pass filter 38a, the detection value detected by the oil degradation/others detection unit 37 is out of the setting range, may be provided.

The motor unit 6 may be provided for each of drive wheels 2. The motor unit 6, together with a wheel bearing unit 4 and the reduction gear unit 7, may form an in-wheel motor drive apparatus 8 that is partly or entirely disposed within the wheel 2. In the case of the in-wheel motor drive apparatus 8, rapid rotation of the wheel bearing unit 4, the reduction gear unit 7, and the motor unit 6 is involved as a result of size reduction of the in-wheel motor drive apparatus 8. Thus, reliability of these components is an urgent concern for the in-wheel motor drive apparatus 8. During the non-traveling period when the vehicle is powered on, any detection item described above is detected by the oil degradation/others detection unit, whereby abnormalities of the oil supply system can be detected. Thus, it is possible to further enhance the reliability of the motor unit and the reduction gear unit.

The reduction gear unit 7 may be in the form of a cycloidal gear device. When the cycloidal gear device is used as the reduction gear unit 7 and the reduction gear ratio is increased, for example to 6 or higher, the size of the motor unit 6 can be reduced, and the size of the apparatus can be reduced. When drive torque of the motor unit 6 is transmitted to the wheel via the reduction gear unit 7 which has a high reduction gear ratio as described above, the drive torque is increased and transmitted to the wheel. Thus, the influence of motor abnormalities caused by heat generation of the motor unit 6 or the like and the influence of insufficient lubrication of the reduction gear unit 7 are increased, but during the non-traveling period of the vehicle, notice of abnormalities of the oil supply system are sent or start of rotation of the motor unit 6 is not permitted when the detection value detected by the oil degradation/others detection unit is out of the setting range, whereby the abnormalities can be recognized at a stage prior to traveling of the vehicle, and it is possible to early deal with the abnormalities.

The electric vehicle according to the present invention is configured to be able to be driven by any motor unit 6 described above.

A diagnostic method according to the present invention is a diagnostic method for a motor unit 6 of an electric vehicle including the motor unit 6 configured to drive a wheel 2; a reduction gear unit 7 configured to produce rotation with a speed that is reduced with respect to that of rotation of the motor unit 6; and an oil supply system configured to supply an oil that is used for any one or both of lubrication of the reduction gear unit 7 and cooling of the motor unit 6. The diagnostic method includes: a detection step of detecting at least any one detection item of a contamination degree, a degradation degree, and an oil amount of the oil during a non-traveling period when the vehicle is powered on; and an abnormalities-time control step of sending notice of abnormalities of the oil supply system or not permitting start of rotation of the motor unit 6 when a detection value detected in the detection step is out of a setting range.

According to this aspect, in the detection step, at least any one detection item of the contamination degree, the degradation degree, and the oil amount of the oil during the non-traveling period when the vehicle is powered on is detected. In the abnormalities-time control step, notice of abnormalities of the oil supply system are sent or start of rotation of the motor unit 6 is not permitted when the detection value is out of the setting range. As described above, for example, as one of checking items in checking abnormalities of the entire vehicle at a stage prior to traveling of the vehicle, etc., or at a time of a stop after start of traveling, abnormalities of the oil supply system can be diagnosed.

The present invention encompasses any combination of at least two features disclosed in the claims, the specification and/or the drawings. In particular, the present invention encompasses any combination of at least two claims.

BRIEF DESCRIPTION OF THE DRAWINGS

In any event, the present invention will become more clearly understood from the following description of embodiments thereof, when taken in conjunction with the accompanying drawings. However, the embodiments and the drawings are given only for the purpose of illustration and explanation, and are not to be taken as limiting the scope of the present invention in any way whatsoever, as defined by the appended claims. In the accompanying drawings, like reference numerals are used to denote like parts throughout the several views, and:

DESCRIPTION OF PREFERRED EMBODIMENTS

Figure 1:
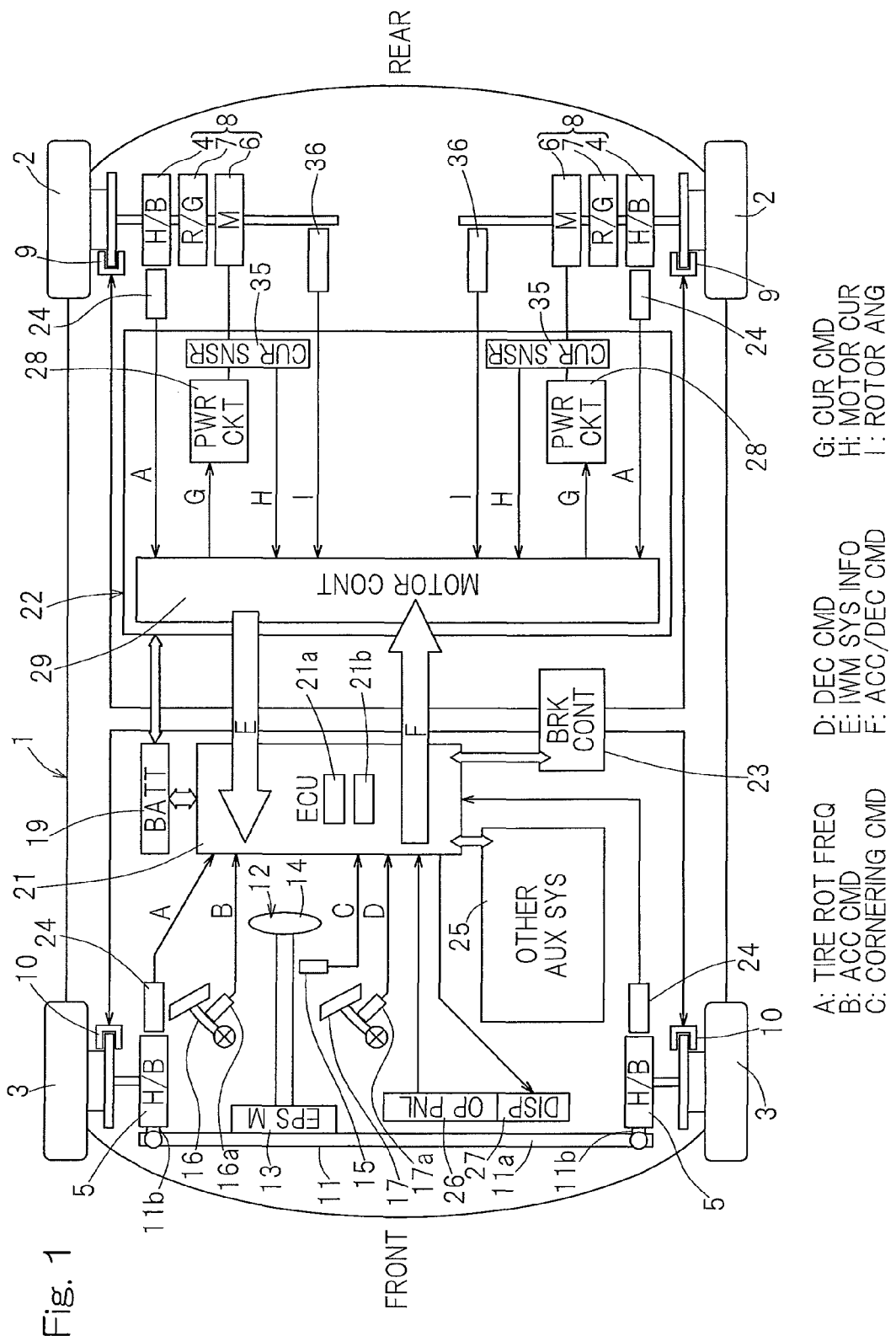
FIG. 1 is a block diagram of a schematic configuration of an electric vehicle equipped with a diagnostic device for a motor unit of an electric vehicle according to one embodiment of the present invention, as viewed from top.
Figure 2:
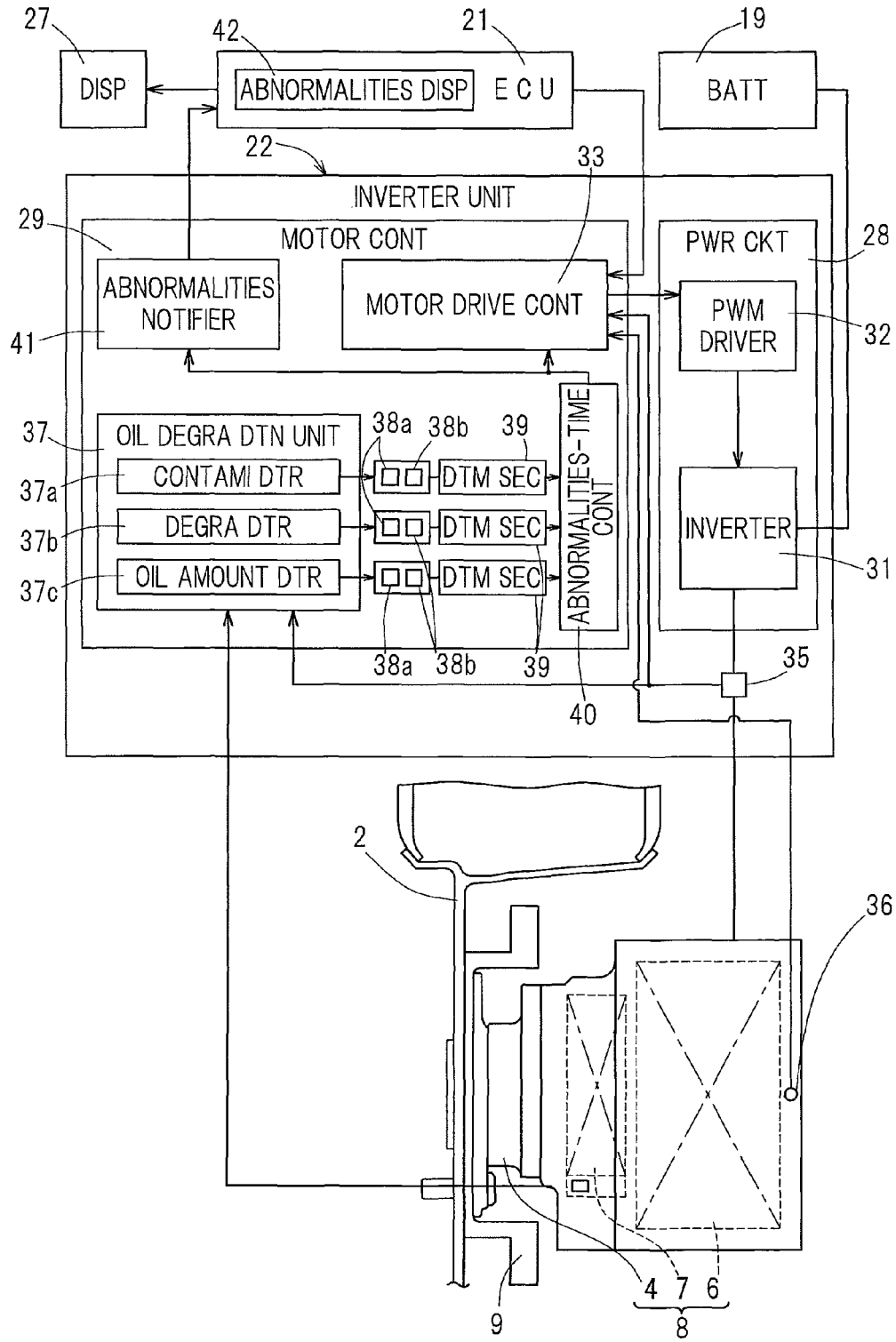
FIG. 2 is a block diagram of a schematic configuration of the diagnostic device for the motor unit of the electric vehicle.

A diagnostic device and a diagnostic method for a motor unit of an electric vehicle according to one embodiment of the present invention will be described in connection with FIGS. 1 to 10. The diagnostic device for the motor unit is installed in the electric vehicle. As shown in FIG. 1, the illustrated electric vehicle is a four-wheel vehicle that includes a vehicle body 1 with left and right rear wheels 2 and left and right front wheels 3, with the rear wheels 2 being drive wheels and the front wheels 3 being steer idler wheels. The drive wheels 2 and the idler wheels 3, both equipped with tires, are supported by the vehicle body 1 via respective wheel bearing units 4, 5. In FIG. 1, the wheel bearing units 4, 5 are labeled with "H/B" which is an abbreviation for hub bearing. The left and right drive wheels 2, 2 are driven by respective independent traction motor units 6, 6. Rotation of the motor unit 6 is transmitted via a reduction gear unit 7 and a wheel bearing unit 4 to a wheel 2. The motor unit 6, the reduction gear unit 7, and the wheel bearing unit 4 are integrally assembled with each other to form an in-wheel motor drive apparatus 8. As shown in FIG. 2, the in-wheel motor drive apparatus 8 is partly or entirely disposed within the drive wheel 2. In the embodiment under discussion, the entireties of the wheel bearing unit 4 and the reduction gear unit 7 and a part of the motor unit 6 overlap the drive wheel 2 along the axis C of the drive wheel 2, but the entirety of the in-wheel motor drive apparatus 8 may overlap the drive wheel 2. The motor unit 6 may, without the interposition of the reduction gear unit 7, directly drive the wheel 2 into rotation. The in-wheel motor drive apparatus 8 may be referred to as an in-wheel motor unit. The wheels 2, 3 are equipped with respective motorised brakes 9, 10.

The left and right front steer wheels 3, 3 are turnable via a turning mechanism 11 and are steered with a steering mechanism 12. The turning mechanism 11 includes left and right knuckle arms 11*b*, 11*b* holding the respective wheel bearing units 5 and also includes a tie rod 11*a* configured to be laterally displaced to change the angles of the left and right knuckle arms 11*b*, 11*b*. An EPS (Electric Power Steering) motor 13 may be driven based on commands from the steering mechanism 12, and the lateral movement of the turning mechanism 11 may be caused via a rotary to linear motion converter mechanism (not shown). A steering angle is detected by a steering angle sensor 15, and output of this sensor is sent to an ECU 21, and the information is used for an accelerating/decelerating command and the like to the left and right wheels.

A control system will be described. As shown in FIG. 1, a controller U1 includes the ECU 21 that is an electric control unit configured to perform general control of the vehicle, and an inverter unit 22 configured to perform control of the traction motor units 6, 6 according to commands from the ECU 21. The ECU 21, the inverter unit 22, and a braking controller unit 23 are installed in the vehicle body 1. The ECU 21 may include a computer, programs that may be executed by the computer, and various electronic circuits.

The ECU 21 may be generally divided, in terms of their functions, into a drive control subunit 21*a* and a general control subunit 21*b*. The drive control subunit 21*a* is configured to generate an accelerating/decelerating signal, which will influence the traction motor units 6, 6 of the left and right wheels, based on an accelerating command produced from an accelerator manipulation unit 16, a decelerating command produced from a brake manipulation unit 17, and a cornering command produced from the steering angle sensor 15, and to send the accelerating/decelerating signal to the inverter unit 22. In addition, the drive control subunit 21*a* may be configured to correct the accelerating/decelerating signal, based on information indicating the rotational frequency of tire(s) produced from rotation sensor(s) 24 that is/are operatively associated with the wheel bearing units 4, 5 for the respective wheels 2, 3 and/or information produced from various sensors that may be mounted to the vehicle. The accelerator manipulation unit 16 includes an accelerator pedal and a sensor 16*a* configured to sense the depression of the accelerator pedal to generate the aforementioned accelerating command. The brake manipulator unit 17 includes a brake pedal and a sensor 17*a* configured to sense the depression of the brake pedal to generate the aforementioned decelerating command.

The general control subunit 21*b* of the ECU 21 is configured to send the decelerating command produced from the brake manipulator unit 17 to the braking controller unit 23, control various auxiliary systems 25, process input commands from an operation panel 26 on a console, cause a display 27 to show information, and/or etc. Examples of the auxiliary systems 25 include an air conditioner, a lamp, a wiper, a GPS, and an airbag. In FIG. 1, the auxiliary systems 25 are indicated in general by a single block.

The braking controller unit 23 is configured to send a braking command to the brakes 9, 10 equipped to the wheels 2, 3, according to the decelerating command received from the ECU 21. Commands related to braking produced from the ECU 21 may include, other than commands generated based on the decelerating command produced from the brake manipulator unit 17, a command generated by a salty improvement subunit that may be included in the ECU 21. The braking controller unit 23 may also include an anti-lock-braking system. The braking controller unit 23 may include electronic circuits and/or a microcomputer.

The inverter unit 22 includes a power circuitry 28, which may be provided one for each of the motor units 6, and a motor control circuitry 29 configured to control the power circuitry/circuitries 28. A common motor control circuitry 29 may be provided for different power circuitries 28. Independent motor control circuitries 29 may be provided for respective different power circuitries 28. Such a common motor control circuitry 29 will be configured to control the different power circuitries 28 independently of each other, for example, to achieve different motor torques. The motor control circuitry 29 may be configured to send various information related to the in-wheel motor drive apparatus 8 (which may be referred to as "IWM system information") held by the motor control circuitry 29, such as a variety of detection values or various control values, to the ECU 21.

FIG. 2 is a block diagram of a schematic configuration of the diagnostic device for the motor unit of the electric vehicle. The illustrated power circuitry 28 includes an inverter 31 configured to convert DC power from a battery unit 19 into three-phase AC power used to drive the motor unit 6 and also includes a PWM driver 32 configured to control the inverter 31. The motor unit 6 may include a three-phase synchronous motor. The inverter 31 may include a plurality of semiconductor switching devices (not shown). The PWM driver 32 may be configured to perform pulse width modulation on a received current command to generate ON/OFF commands to the semiconductor switching devices.

The motor control circuitry 29 may include a computer, programs that may be executed by the computer, and various electronic circuits. The motor control circuitry 29 may include a motor drive controller 33 which serves as a basic control component. The motor drive controller 33 may be configured to receive the accelerating/decelerating command such as a torque command from the ECU which serves as an upper-level control unit, convert the accelerating/decelerating command into a current command, and send the current command to the PWM driver 32 of the power circuitry 28. The motor drive controller 33 may be configured to obtain a value of motor current that flows from the inverter 31 to the motor unit 6, with a current sensor 35, and perform a current feedback control. In addition, the motor drive controller 33 may be configured to obtain a rotational angle of a rotor of the motor unit 6, with an angle sensor 36, and perform control, such as a vector control, in accordance with the rotational angle.

The diagnostic device for the motor unit 6 will be described. In the embodiment under discussion, as shown in FIG. 2, the motor control circuitry 29 configured as described above includes an oil degradation/others detection unit 37, low-pass filters 38*a*, detection circuits 38*b*, determining sections 39, an abnormalities-time control unit 40, and an abnormalities notifier 41, and the ECU 21 includes an abnormalities display 42. The diagnostic device for the motor unit 6 according to the embodiment under discussion includes the oil degradation/others detection unit 37, the low-pass filters 38*a*, the detection circuits 38*b*, the determining sections 39, the abnormalities-time control unit 40, the abnormalities notifier 41, and the abnormalities display 42. In this example, the electric vehicle includes an oil supply system (described later in connection with FIGS. 8 to 10) configured to supply an oil used for both lubricating the reduction gear unit 7 and cooling the motor unit 6.

The oil degradation/others detection unit 37 is configured to detect at least any one detection item of a contamination degree, a degradation degree, and an oil amount of the oil, which lubricates the reduction gear unit 7 and cools the motor unit 6, during a non-traveling period when the vehicle is powered on. The "non-traveling period when the vehicle is powered on" refers to a state where the ECU 21 of the electric vehicle is powered on and the vehicle completely stops, and, for example, refers to (1) a time when a driver or the like operates a start-up unit such as a key or a start button from "OFF" to a position of "accessory power", which is prior to power supply to each motor unit 6, to turn on the ECU 21, (2) a case where the start-up unit is operated to a position of "ON" in a state where the ECU 21 is ON but the ECU 21 does not generate an accelerating command to the motor unit 6, and a time when it is determined that the vehicle is in a state where travelling thereof is stopped, based on information indicating the rotational frequency of tire(s) produced from the rotation sensor(s) 24, information produced from various sensors that may be mounted to the vehicle, and/or the like, but a lock state where a minute current flows to the ECU 21 and the ECU 21 is ON but a driver or the like does not get in the vehicle and security for the vehicle is ON, is not included.

In addition, the oil degradation/others detection unit 37 is configured to detect the detection item of the oil after elapse of a time period or longer during which time period air mixed in the oil is being released out of the oil. For example, immediately after a stop after start of traveling, it is in a state where air is mixed in the oil. Thus, the oil degradation/others detection unit 37 is configured to detect the detection item of the oil after elapse of the time period or longer during which time period the air mixed in the oil is being released out of the oil. The time period is set based on an experiment or the like.

When the start-up unit is at the position of "accessory power" or "ON", it is determined that the ECU 21 is ON. When it is determined that the ECU 21 is ON and it is determined that power supply to each motor unit 6 is not performed, based on the motor current from each current sensor 35, the information indicating the rotational frequency of tire produced from each rotation sensor 24, information produced from various sensors that may be mounted to the vehicle, and/or the like, it is determined that it is during the non-traveling period when the vehicle is powered on.

In this example, the oil degradation/others detection unit 37 includes a contamination degree detector 37a configured to detect the contamination degree of the oil, a degradation degree detector 37b configured to detect the degradation degree of the oil, and an oil amount detector 37c configured to detect the oil amount. The determining sections 39 are provided which determine whether the detection values detected by the respective detectors 37a, 37b, and 37c are out of setting ranges. When any determining section 39 determines that the detection value is out of the setting range, the abnormalities-time control unit 40 sends notice of abnormalities of the oil supply system and performs control such that start of rotation of each motor unit 6 is not permitted.

Figure 3:
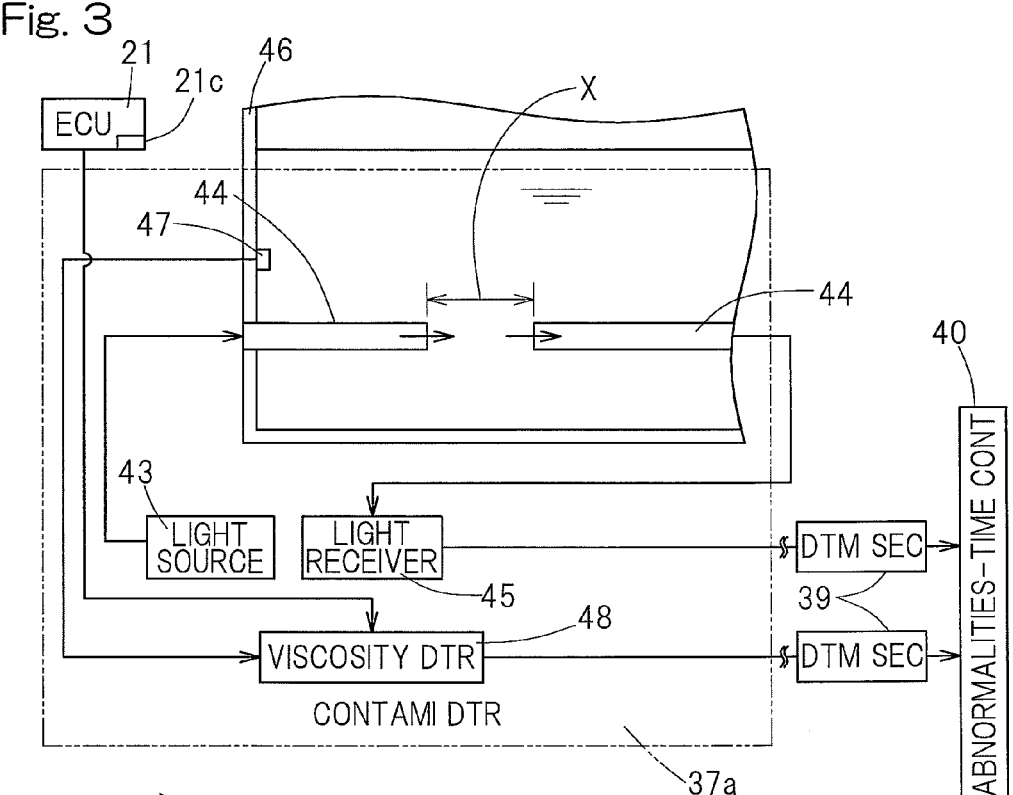
FIG. 3 is a block diagram of a contamination degree detector and the like of the diagnostic device.
Figure 4:
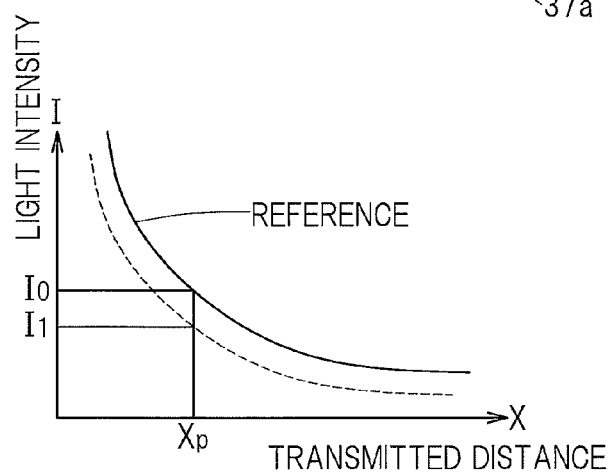
FIG. 4 is a graph showing a relationship between the transmitted distance of light transmitted through an oil and the intensity of the transmitted light.

FIG. 3 is a block diagram showing the contamination degree detector and the like of the diagnostic device. As shown in FIG. 3, the contamination degree detector 37a includes a light source 43, optical fibers 44, 44 configured to guide light emitted from the light source 43 into the oil and further to a light receiver 45, and the light receiver 45 that is a measurer configured to measure the light transmittance in the oil for the light guided by the optical fibers 44, 44. As the light source 43, for example, a light-emitting diode, an incandescent lamp, a semiconductor laser diode, an electroluminescence abbreviated as EL, an organic EL, a fluorescent tube, or the like may be used. As the light receiver 45, for example, a photodiode, a phototransistor, a solar battery, a photomultiplier, or the like may be used.

A cause for contamination of the oil is an increasing amount of contaminants such as abrasion powder in the oil. When the amount of contaminants in the oil is increased, the light transmittance is changed. Thus, the contamination degree of the oil is detected by measuring the light transmittance in the oil. The intensity of the light transmitted through the oil is greatly attenuated depending on the distance by which the light is transmitted. The transmitted light intensity and the transmitted distance have a relationship shown in a graph in FIG. 4. The relationship is:

$$I = I_{in} \cdot \exp(-\alpha x) \quad (1),$$

where the transmitted light intensity, namely, the transmitted light amount, is I, the transmitted distance is x, an amount of light incident on the oil is $I_{in}$, and $\alpha$ is a constant. The value of the constant $\alpha$ in the above formula (1) is changed depending on the state of the oil. For example, when foreign matter such as abrasion powder is mixed into the oil with rotation of the reduction gear unit 7, the constant $\alpha$ is increased as the mixed amount of the foreign matter is increased. In addition, when the oil is degraded, oxidation and discoloration of the oil proceed. Thus, the constant $\alpha$ is increased as the degradation state proceeds. Therefore, when an amount of light incident from the light source 43 and a transmitted distance are previously set as appropriate based on a test and a transmitted light intensity immediately after oil replacement in the oil supply system is previously stored, a light transmittance can be measured by obtaining the ratio of a detected transmitted light intensity $I_1$ to a transmitted light intensity $I_0$ as a reference (detected transmitted light intensity $I_1$/transmitted light intensity $I_0$ as the reference).

As shown in FIG. 3, the oil supply system includes a tank 46 configured to store therein the oil used for lubricating the reduction gear unit 7 and cooling the motor unit 6. Within the tank 46, ends of the respective optical fibers 44 are provided so as to be opposed to and spaced apart from each other by the transmitted distance x. The optical fibers 44 are provided in the tank 46 such that the oil is present between the ends of the optical fibers 44. The light emitted from the light source 43 travels through one of the optical fibers 44, passes through the oil present in the tank 46, travels through the optical fiber 44 on the other side, and is detected by the light receiver 45. In the light receiver 45, the ratio $I_1/I_0$ of the detected transmitted light intensity $I_1$ to the transmitted light intensity $I_0$ as the reference is obtained and a light transmittance is measured. The measured light transmittance is photoelectrically converted to an electric signal which is a detection value, and the detection value is used for later-described determination by the determining section 39.

It is to be noted that a plurality of optical fibers 44 may be provided on each of both sides of the oil, which is a detection target, so as to be opposed to the optical fibers 44 on the other side of the oil such that end surfaces thereof are arranged in a linear manner or in a planar manner. In this case, a sufficient light-receiving surface area can be ensured on the light reception side, and thus a sufficient received light intensity can be obtained by the light receiver 45. Therefore, the light transmittance can be stably measured by the light receiver 45.

Figure 5:
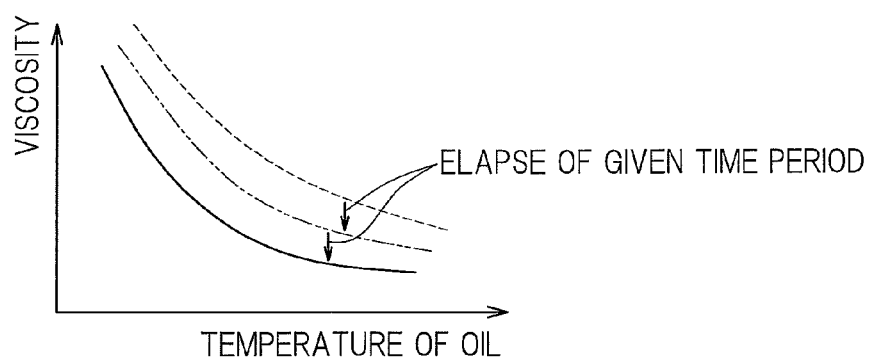
FIG. 5 is a graph showing a relationship between the temperature and the viscosity of the oil.

As shown in FIG. 3, the contamination degree detector 37a includes an oil temperature detector 47 configured to detect the temperature of the oil, and a viscosity detector 48 configured to obtain the viscosity of the oil based on the temperature of the oil detected by the oil temperature detector 47. Here, FIG. 5 is a graph showing a relationship between the temperature and the viscosity of the oil. In general, the viscosity of an oil is decreased as the temperature of the oil is increased. In addition, an oil viscosity after elapse of a given time period after oil replacement is lower than an oil viscosity immediately after the oil replacement. Regarding the oil after the elapse of the given time period after the oil replacement, degradation and contamination of the oil can be regarded as having proceeded. Thus, the relationship, shown in FIG. 5, between the temperature and the viscosity of the oil for every given time period is previously stored as a table or the like, and the viscosity detector 48 can obtain an oil viscosity by checking the temperature of the oil detected by the oil temperature detector 47 and an elapsed time at the detection against the table or the like. Therefore, the contamination degree of the oil can be detected based on the obtained oil viscosity. It is to be noted that the ECU 21 includes a clock source 21c such as a crystal oscillator or an oscillating circuit, and the clock source 21c is configured to count a time elapsed after oil replacement. An operator is allowed to reset the elapsed time each time the oil is replaced, by accessing the ECU 21, for example, using a computer or the like.

When the oil is degraded due to, for example, water being mixed into the oil, the dielectric constant among the electric characteristics of the oil is greatly changed.

Figure 6:
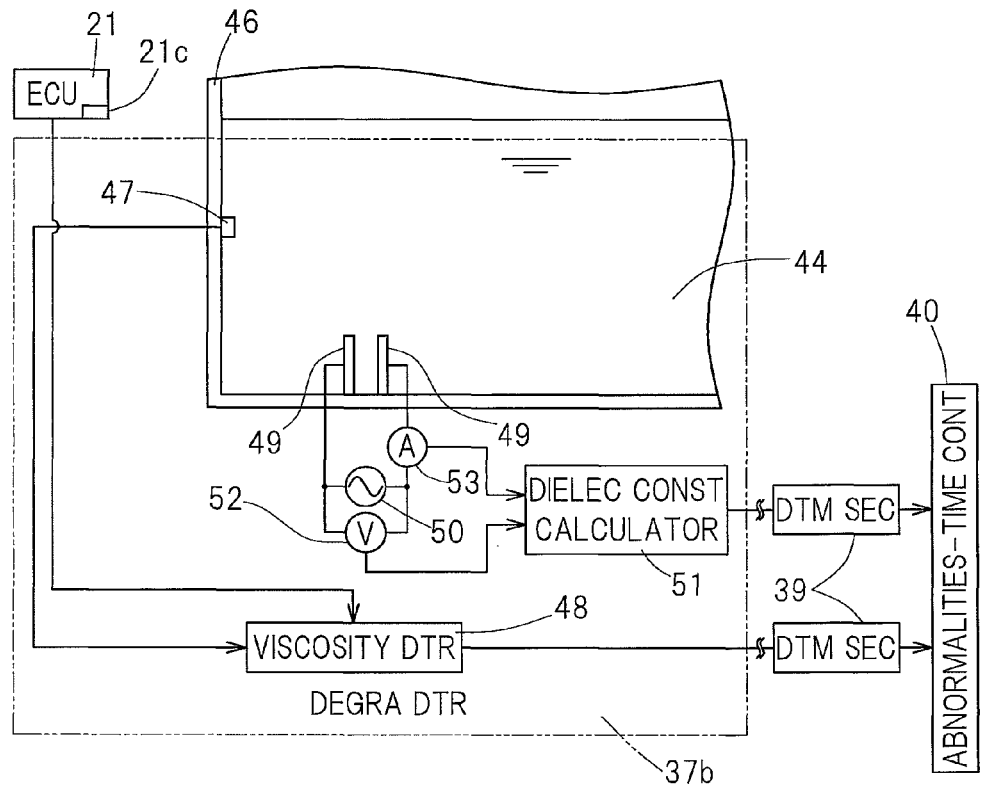
FIG. 6 is a block diagram of a degradation degree detector and the like of the diagnostic device.

As shown in FIG. 6, the degradation degree detector 37b includes two electrodes 49, 49 provided within the oil so as to be spaced apart from each other, a detection power source 50 configured to apply an AC voltage between the electrodes 49, 49, and a dielectric constant calculator 51 configured to obtain a dielectric constant of the oil when the AC voltage is applied between the two electrodes 49, 49 by the detection power source 50. Here, as an equivalent circuit of the electrodes 49, 49 and the oil present between the electrodes 49, 49, a parallel circuit is assumed in which a capacitance C and a resistance R are connected in parallel. The capacitance C corresponds to the capacitance value of the oil present between the electrodes 49, 49. Since the interval between the two electrodes 49, 49 and the surface areas of the flat surfaces of the electrodes 49, 49 are known, the dielectric constant calculator 51 can obtain the dielectric constant ∈ of the oil from the capacitance C of the oil present between the electrodes 49, 49 and the resistance R between the electrodes 49, 49. The resistance R between the electrodes 49, 49 can be obtained by a voltage sensor 52 configured to measure the applied AC voltage and a current sensor 53 configured to measure a current that flows when the AC voltage is applied between the electrodes 49, 49.

It is possible to detect the degradation degree of the oil based on the dielectric constant ∈ of the oil obtained by the dielectric constant calculator 51. It is to be noted that the degradation degree detector 37*b* may include the oil temperature detector 47 and the viscosity detector 48 described above. In addition, as shown in FIG. 2, the oil amount detector 37*c* is composed of a magnetic, optical, electrode, or ultrasonic liquid level sensor used for controlling a liquid level. The liquid level sensor is provided within the tank 46 (FIG. 6), and the determining section 39 determines whether the liquid level falls between an upper limit and a lower limit determined within the tank 46, during a non-traveling period when the vehicle is not powered on.

Figure 7:
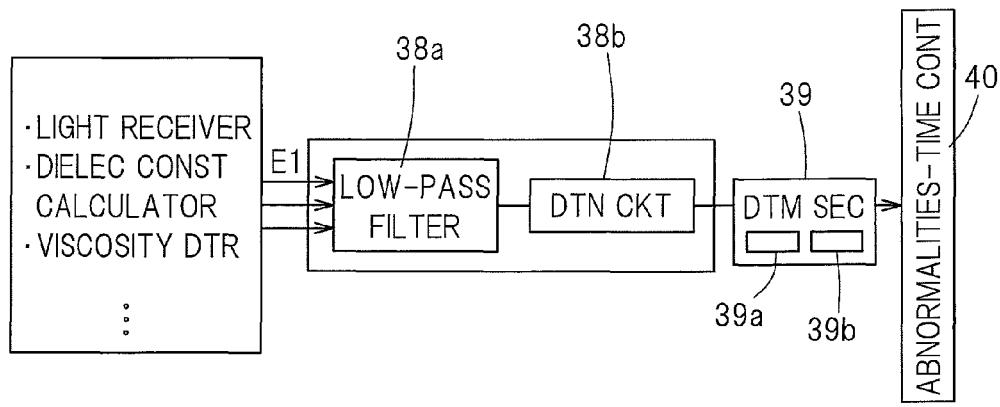
FIG. 7 is a block diagram of a principal part of the diagnostic device.

FIG. 7 is a block diagram of a principal part of the diagnostic device. The diagnostic device includes the low-pass filter 38*a* and the detection circuit 38*b*. As shown in FIG. 7, each of the detection values detected by the contamination degree detector 37*a*, the degradation degree detector 37*b*, and the oil amount detector 37*c* described above is processed through the low-pass filter 38*a*, and a signal having passed through the low-pass filter 38*a* is detected by the detection circuit 38*b*. The cut-off frequency of the low-pass filter 38*a* is set as appropriate, for example, in accordance with the configuration of the in-wheel motor drive apparatus 8, and is, for example, several tens Hz.

The determining section 39 includes a range definer 39*a* configured to define a setting range in accordance with each detection value, and a comparator 39*b*. The comparator 39*b* is configured to compare the detection value outputted from the detection circuit 38*b* with the setting range and determine whether the detection value exceeds the setting range. An electric signal E1 obtained by photoelectrically converting the light transmittance measured by the light receiver 45 is outputted through the low-pass filter 38*a* and the detection circuit 38*b*.

The comparator 39*b* is configured to compare the outputted detection value with the setting range. The setting range in this case is defined as appropriate based on an experiment, a simulation, or the like. For example, a value obtained by outputting, through the low-pass filter 38*a* and the detection circuit 3 8*b*, an electric signal when the temperature of the oil detected by the oil temperature detector 47 after the motor unit 6 is rotated at a specified rotational frequency for a given time period and travelling is stopped is not decreased to a desired temperature or lower, is set as a setting range.

The dielectric constant ∈ of the oil calculated by the dielectric constant calculator 51 is outputted through the low-pass filter 38*a* and the detection circuit 38*b*, and this outputted detection value and a setting range are compared with each other by the comparator 39*b*. The setting range in this case is also defined as appropriate based on an experiment, a simulation, or the like, similarly to the above. For example, a value obtained by outputting, through the low-pass filter 38*a* and the detection circuit 38*b*, an electric signal which is proportional to the dielectric constant ∈ when the temperature of the oil detected by the oil temperature detector 47 after the motor unit 6 is rotated at a specified rotational frequency for a given time period and travelling is stopped is not decreased to a desired temperature or lower, is set as a setting range. A setting range in the case of comparing the oil amount or the oil viscosity is also defined similarly.

Upon receiving, from the comparator 39*b*, a signal indicative of exceeding the setting range, the abnormalities-time control unit 40 sends notice of abnormalities of the oil supply system or performs control such that start of rotation of the motor unit 6 is not permitted. As shown in FIG. 2, the abnormalities notifier 41 receives, from the abnormalities-time control unit 40, a signal indicating the abnormalities of the oil supply system, and sends information indicating the abnormalities to the ECU 21. Upon receiving the signal, the motor drive controller 33 limits a motor torque command or a motor current produced from the inverter unit 22, whereby start of rotation of the motor unit 6 is not permitted.

Advantageous effects will be described. During the non-traveling period when the vehicle is powered on, specifically, when a driver or the like operates the start-up unit such as a key or a start button from "OFF" to the position of "accessory power" at which it is possible to actuate the auxiliary systems 25 such as a lamp and a wiper, to turn on the ECU 21, the oil degradation/others detection unit 37 detects at least any one detection item of the contamination degree, the degradation degree, and the oil amount of the oil. During such a non-traveling period when the vehicle is powered on, it is possible to reduce bubbling of the oil by stopping rotation of the reduction gear unit 7, and thus the contamination degree, the degradation degree, and the oil viscosity of the oil can be easily and accurately measured.

Furthermore, the oil degradation/others detection unit 37 detects the detection item of the oil after elapse of the time period or longer during which time period air mixed in the oil is being released out of the oil. Thus, for example, erroneous detection in a state where air is mixed in the oil immediately after a stop after start of traveling can be prevented. Therefore, the contamination degree, the degradation degree, and the oil viscosity of the oil can be more accurately measured. In addition, during the non-traveling period, rotation of the reduction gear unit 7 is stopped, and rotation of a rotary pump 54 (FIG. 8) of the oil supply system is also stopped. Thus, circulation of the oil is stopped, and it is possible to stabilize the oil in the tank 46 without ruffling the surface of the oil. Thus, the amount of the oil in the tank 46 can be accurately detected by the oil amount detector 37*c*.

When the measured detection value is out of the setting range, the abnormalities-time control unit 40 sends notice of abnormalities of the oil supply system and performs control such that start of rotation of the motor unit 6 is not permitted. As described above, for example, as one of checking items in checking abnormalities of the entire vehicle at a stage prior to traveling of the vehicle, etc., or at a time of a stop after start of traveling, abnormalities of the oil supply system can be diagnosed. When notice of abnormalities of the oil supply system are sent, or when start of rotation of the motor unit 6 is not permitted, the oil supply system and the like are to be repaired, or rescue of the vehicle can be requested.

The ends of the respective optical fibers 44 are provided within the tank 46 as shown in FIG. 3, and the electrodes 49, 49 are provided within the tank 46 as shown in FIG. 6. In this manner, the detector can be easily installed within the tank 46. The oil can be stored within the tank 46. Thus, in any of a time of start-up and a time of stopping traveling, abnormalities of the oil supply system can be stably diagnosed.

Figure 8:
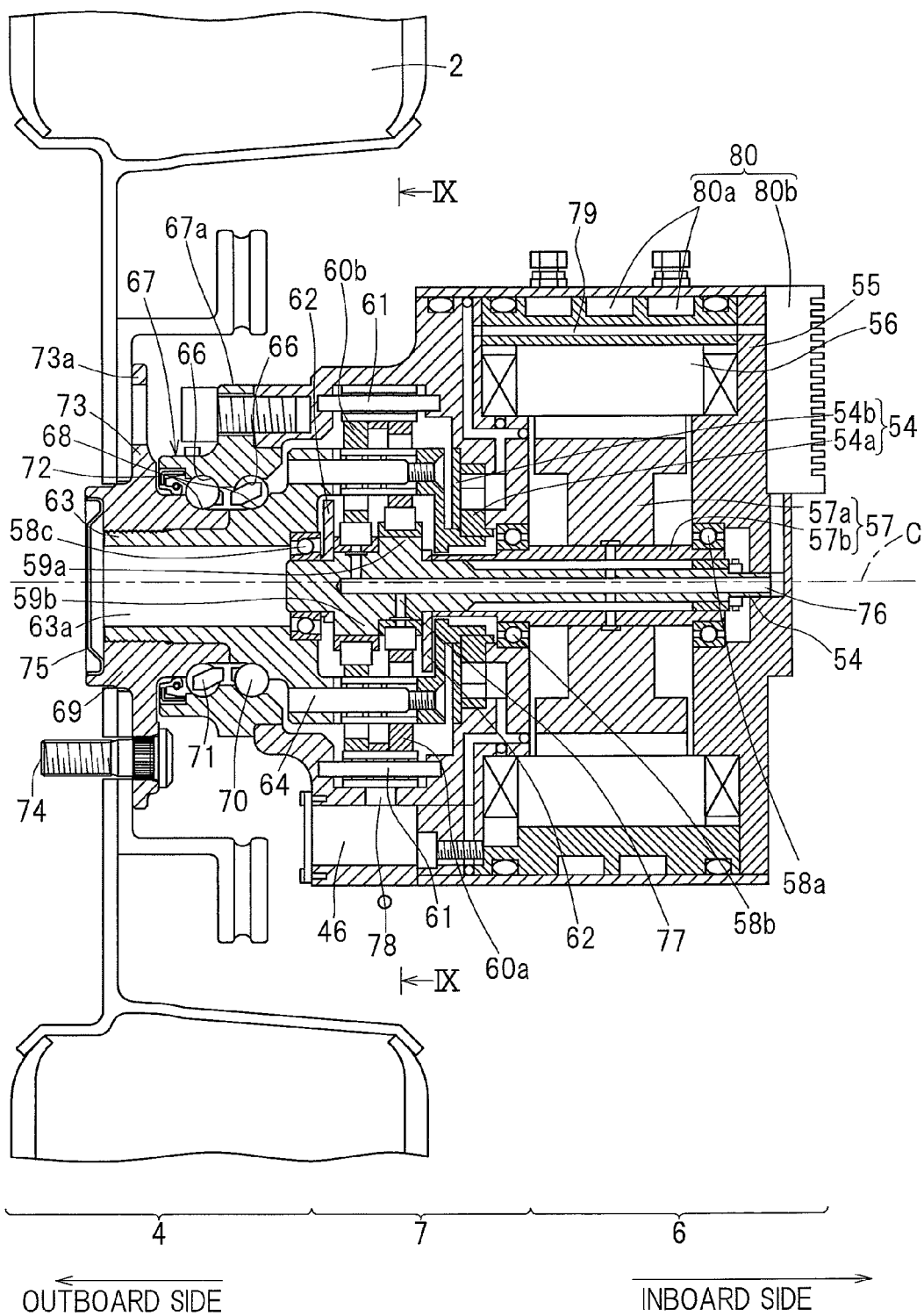
FIG. 8 is a front cut-away view of an in-wheel motor drive apparatus for the electric vehicle.

FIG. 8 is a front cut-away view of the in-wheel motor drive apparatus 8 in the electric vehicle. As shown in FIG. 8, the in-wheel motor drive apparatus 8 includes the wheel bearing unit 4, the motor unit 6, and the reduction gear unit 7 interposed between the wheel bearing unit 4 and the motor unit 6, in which a hub of the wheel 2 (FIG. 2) which is the drive wheel supported by the wheel bearing unit 4 is coaxially coupled with a motor-side rotary member 54 of the motor unit 6 (FIG. 8). It is to be noted that hereinafter in this specification, terms "outboard" and "inboard" represent one side of the vehicle body away from the longitudinal center of the vehicle body and the other side of the vehicle body close to the longitudinal center of the vehicle body, respectively, when assembled in the vehicle body.

The motor unit 6 includes a radial-gap type, IPM motor (i.e., a buried magnet type synchronous motor) that includes a motor stator 56 fixed to a cylindrical motor housing 55 and also includes a motor rotor 57 mounted to the motor-side rotary member 54, with a radial gap provided between the motor stator 56 and the motor rotor 57. The rotor 57 includes a rotor portion 57a and a cylindrical hollow portion 57b. The motor-side rotary member 54 is provided within the rotor 57, is coupled with the rotor 57, and co-rotates with the rotor 57. The motor-side rotary member 54 transmits a drive force of the motor unit 6 to the reduction gear unit 7. Bearing units 58a, 58b are provided in the motor housing 55 so as to be axially spaced apart from each other, and the hollow portion 57b is fitted to these bearing units 58a, 58b. Thus, the rotor 57 is rotatably supported by the motor housing 55.

The motor-side rotary member 54 is disposed so as to extend from the motor unit 6 to the reduction gear unit 7, and includes eccentric segments 59a, 59b within the reduction gear unit 7. The motor-side rotary member 54 is fitted at its end on the motor unit 6 side to the hollow portion 57b of the rotor 57 and is supported at its other end on the reduction gear unit 7 side by a bearing unit 58c. The eccentric segments 59a, 59b are provided, 180° out of phase with each other, such that the centrifugal forces caused by eccentric motions of the eccentric segments 59a, 59b can be cancelled.

Figure 9:
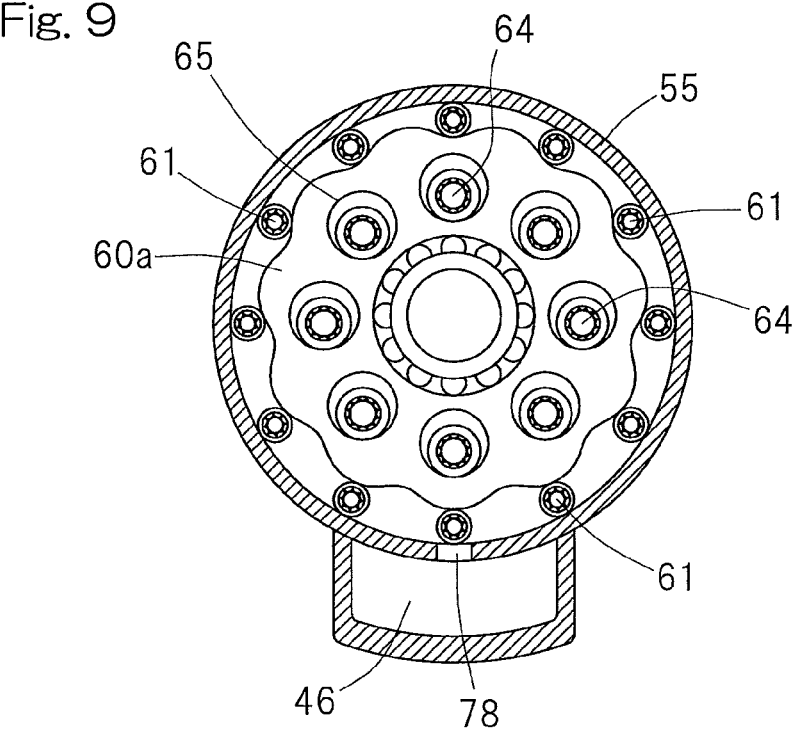
FIG. 9 is a cross-sectional view of a reduction gear unit part, taken along the line IX-IX in FIG. 8.

The reduction gear unit 7 preferably has a reduction gear ratio of 6 or higher. The reduction gear unit 7 includes curvilinear plates 60a, 60b, a plurality of outer pins 61, a motion converter mechanism, and counterweights 62, 62. The curvilinear plates 60a, 60b are rotatably provided to the eccentric segments 59a, 59b, respectively. The plurality of outer pins 61 are supported by the motor housing 55 so as to be in rolling contact with the outer peripheries of the curvilinear plates 60a, 60b. The motion converter mechanism is configured to transmit rotation motions of the curvilinear plates 60a, 60b to an inboard member 63. In other words, as shown in FIGS. 8 and 9, the motion converter mechanism includes a plurality of inner pins 64 provided to the inboard member 63 and through holes 65 formed in the curvilinear plates 60a, 60b. The inner pins 64 are circumferentially disposed at equal intervals around the rotation axis of the inboard member 63 as a center. An axial end portion of each inner pin 64 is screwed into and fixed to the inboard member 63. The counterweights 62, 62 are provided at respective axial locations, in the motor-side rotary member 54, adjacent to the eccentric segments 59a, 59b.

The wheel bearing unit 4 includes an outer member 67 having an inner periphery formed with a plurality of rows of raceway surfaces 66, an inner member 69 having an outer periphery formed with raceway surfaces 68 held in face to face relation to those raceway surfaces 66, and a plurality of rows of rolling elements 70 that are interposed between the raceway surfaces 66 of the outer member 67 and the raceway surfaces 68 of the inner member 69. The inner member 69 concurrently serves as a hub for mounting a drive wheel. The illustrated wheel bearing unit 4 includes a double row angular contact ball bearing, in which the rolling elements 70 are in the form of balls rollingly retained by a retainer 71 that is provided one for each row of the balls. The raceway surfaces 66, 68 have arcuate cross sectional shapes and are formed to have respective contact angles held in back-to-back relation with each other. The outer member 67 and the inner member 69 define a bearing space therebetween, and an outboard end of the bearing space is sealed by a sealing member 72.

The outer member 67, which serves as a stationary member, is of one piece construction having a flange 67a for attaching to an outboard housing of the reduction gear unit 7. The flange 67a has bolt insertion holes formed at a plurality of circumferential locations thereof. The housing has bolt receiving holes that are internally threaded at locations thereof corresponding to the respective bolt insertion holes. The outer member 67 can be mounted to the housing by screwing into the bolt receiving holes the mounting bolts that are pre-inserted in the bolt insertion holes.

The inner member 69, which serves as a rotational member, includes an outboard member 73 having a hub flange 73a for attaching a wheel. The inner member 69 also includes the inboard member 63 which has an outboard side fitted to an inner periphery of the outboard member 73 and which is crimped to be integrated with the outboard member 73. The outboard member 73 and the inboard member 63 have the corresponding rows of the raceway surfaces 68 formed thereon. The inboard member 63 has a center thereof formed with a through bore 63a. The hub flange 73a has press fitting holes at a plurality of circumferential locations thereof for receiving corresponding hub bolts 74. The outboard member 73 has a cylindrical pilot portion for guiding the drive wheel and brake components (not shown), which is located in the vicinity of the root of the hub flange 73a of the outboard member 73 and is protruding towards the outboard side. A cap 75 closing an outboard end of the through bore 63a is fitted to an inner periphery of the pilot portion.

Figure 10:
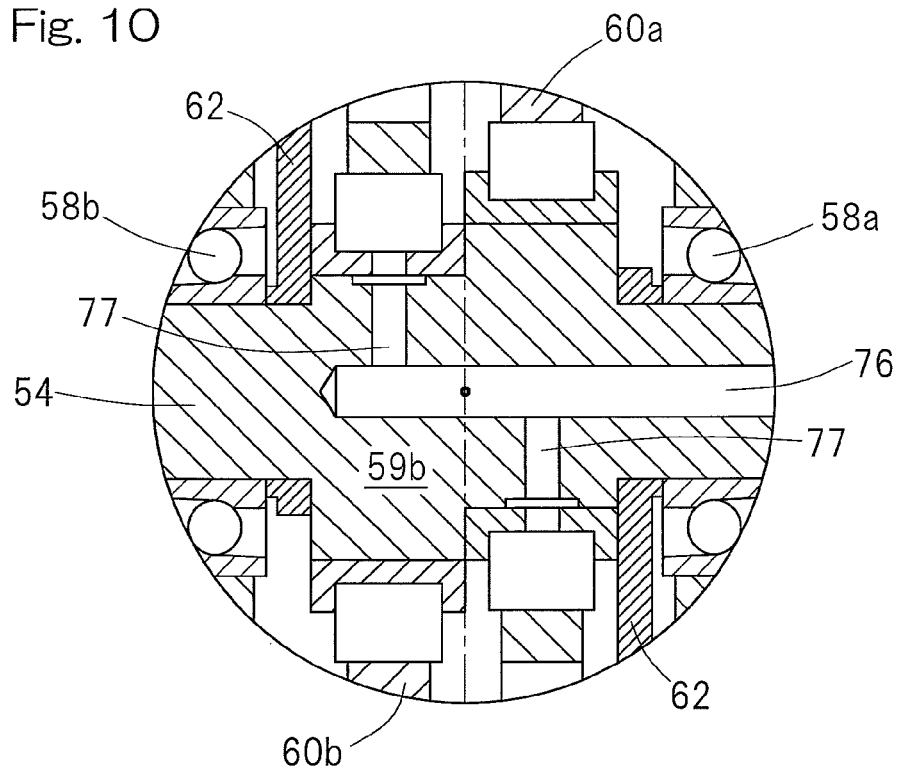
FIG. 10 is a partially enlarged view of a principal part of FIG. 8.

The oil supply system will be described. As shown in FIGS. 8 and 10, the oil supply system includes an oil passage 76, oil supply ports 77, an oil discharge port 78, the tank 46, the rotary pump 54, a circulating oil passage 79, and a cooling unit 80. The oil passage 76 extends within the motor-side rotary member 54 from an inboard side end thereof toward the outboard side in the axial direction. As shown in FIG. 10, the oil supply ports 77 extend from axial locations, in the oil passage 76, where the eccentric segments 59a, 59b are provided, toward an outer diameter surface of the motor-side rotary member 54 outwardly in the radial direction.

As shown in FIG. 9, the oil discharge port 78 is provided at at least one position in an axial location, in the motor housing 55, where the reduction gear unit 7 is provided. The oil discharge port 78 is used for discharging the oil within the reduction gear unit therethrough. As shown in FIG. 8, the circulating oil passage 79 is configured to return the oil discharged through the oil discharge port 78, to the oil passage 76.

The rotary pump 54 is provided on an oil passage between the oil discharge port 78 and the circulating oil passage 79, and is configured to forcibly circulate the oil. The rotary pump 54 is, for example, a cycloidal pump that includes: an inner rotor 54a which rotates with rotation of the inboard member 63; an outer rotor 54b which rotates in a following manner with rotation of the inner rotor 54a; a pump chamber which is not shown; an inlet which communicates with the oil discharge port 78; and an outlet which communicates with the circulating oil passage 79.

When the inner rotor 54*a* rotates with rotation of the inboard member 63, the outer rotor 54*b* rotates in a following manner. Since the inner rotor 54*a* and the outer rotor 54*b* rotate about different rotation axes at that time, the volume of the pump chamber is continuously changed. Thus, the oil flowing in through the inlet is pressure-fed through the outlet to the circulating oil passage 79.

The tank 46 is provided on an oil passage between the oil discharge port 78 and the rotary pump 54 and is configured to temporarily store the oil therein. During high-speed rotation, the oil that cannot be discharged by the rotary pump 54 is stored in the tank 46, whereby an increase in loss of the torque of the reduction gear unit 7 can be prevented. During low-speed rotation, even when the amount of the oil that reaches the oil discharge port 78 is decreased, the oil stored in the tank 46 is returned to the oil passage 79, whereby the oil can be stably supplied to the reduction gear unit 7. The tank 46 is mounted at an axial location, in the motor housing 55, where the reduction gear unit 7 is provided. The oil lubricating the inside of the reduction gear unit 7 is moved outwardly in the radial direction and downwardly by the centrifugal force and the gravitational force. Therefore, in this example, the tank 46 is mounted below the in-wheel motor drive apparatus 8.

The cooling unit 80 is configured to cool the motor unit 6 and the oil passing through the circulating oil passage 79, and includes cooling water passages 80*a* formed in the motor housing 55 and a heat sink 80*b* mounted on the motor housing 55.

Other embodiments of the abnormalities-time control unit 40, the oil degradation/others detection unit 37, and the like in the above-described embodiment will be described below. Specifically, the abnormalities-time control unit 40 shown in FIG. 2 sends notice of abnormalities to the abnormalities notifier 41 and performs control such that start of rotation of the motor unit 6 is not permitted, but may be configured to perform either one of them. The oil degradation/others detection unit 37 shown in FIG. 2 includes the contamination degree detector 37*a*, the degradation degree detector 37*b*, and the oil amount detector 37*c*, but is not necessarily limited to this configuration. The oil degradation/others detection unit 37 may be configured to include any one of the three components, that is, the contamination degree detector 37*a*, the degradation degree detector 37*b*, and the oil amount detector 37*c*, or may be configured to include any two of them.

The tank 46 of the oil supply system shown in FIG. 8 may be provided as a member separate from the motor housing 55, and may be connected to the motor housing 55 via a pipe. In addition, the oil supply system in FIG. 8 may be used only for lubricating the reduction gear unit 7 or can be used only for cooling the motor unit 6.

Although the present invention has been described in connection with preferred embodiments with reference to the accompanying drawings which are used only for the purpose of illustration, those skilled in the art will readily conceive numerous changes and modifications within the framework of obviousness upon the reading of the specification herein presented of the present invention. Accordingly, such changes and modifications are, unless they depart from the scope of the present invention as delivered from the claims annexed hereto, to be construed as included therein.

REFERENCE NUMERALS 2, 3: Wheel
6: Motor unit
7: Reduction gear unit
8: In-wheel motor drive apparatus
21: ECU
24: Rotation sensor
35: Current sensor
37: Oil degradation/others detection unit
37*a*: Contamination degree detector
37*b*: Degradation degree detector
38*a*: Low-pass filter
39: Determiner
40: Abnormalities-time control unit
43: Light source
44: Optical fiber
45: Light receiver
46: Tank
47: Oil temperature detector
48: Viscosity detector
49: Electrode
50: Detection power source

What is claimed is:

1. A diagnostic device for a motor unit of an electric vehicle including the motor unit configured to drive a wheel; a reduction gear unit configured to produce rotation with a speed that is reduced with respect to that of rotation of the motor unit; and an oil supply system having a pump configured to supply an oil that is used for both of lubrication of the reduction gear unit and cooling of the motor unit, the diagnostic device comprising: an oil detection unit configured to detect at least any one detection item of a contamination degree and a degradation degree of the oil only during a non-traveling period, the non-traveling period including a time of start-up and a time of stopping travelling, when the vehicle is powered on but power is not supplied to the motor unit from a control unit and the motor unit and the pump are not rotating;

a motor drive controller configured to receive a motor torque command from the control unit or obtain a value of motor current that flows from an inverter to the motor unit using a current sensor;

an abnormalities-time control unit, directly coupled to the motor drive controller, configured to send notice of abnormalities of the oil supply system and not permit start of rotation of the motor unit when a detection value detected by the oil detection unit is out of a setting range; and upon receiving the signal of abnormalities, the motor drive controller limits the motor torque command or the motor current produced from the inverter, whereby start of rotation of the motor unit is not permitted.

2. The diagnostic device for the motor unit of the electric vehicle as claimed in claim 1, wherein the oil detection unit detects the detection item of the oil after elapse of a time period or longer during which time period air mixed in the oil is being released out of the oil.

3. The diagnostic device for the motor unit of the electric vehicle as claimed in claim 1, wherein the oil supply system includes a tank configured to store the oil therein, and
the oil detection unit includes a detector provided within the tank.

4. The diagnostic device for the motor unit of the electric vehicle as claimed in claim 1, wherein the oil detection unit includes a contamination degree detector configured to detect the contamination degree of the oil, and
the contamination degree detector includes a measurer configured to measure a light transmittance in the oil.

5. The diagnostic device for the motor unit of the electric vehicle as claimed in claim 1, wherein the oil detection unit includes a degradation degree detector configured to detect the degradation degree of the oil, and the degradation degree detector includes two electrodes provided within the oil so as to be spaced apart from each other, a detection power source configured to apply an AC voltage between these electrodes, and a dielectric constant calculator configured to obtain a dielectric constant of the oil when the AC voltage is applied between the two electrodes by the detection power source.

6. The diagnostic device for the motor unit of the electric vehicle as claimed in claim 1, wherein the oil detection unit includes an oil temperature detector configured to detect a temperature of the oil, and a viscosity detector configured to obtain a viscosity of the oil based on the temperature of the oil detected by the oil temperature detector.

7. The diagnostic device for the motor unit of the electric vehicle as claimed in claim 1, further comprising:

a determining section configured to determine whether a value obtained by processing, through a low-pass filter, the detection value detected by the oil detection unit is out of the setting range.

8. An electric vehicle comprising:

a motor unit configured to drive a wheel;

a reduction gear unit configured to produce rotation with a speed that is reduced with respect to that of rotation of the motor unit;

an oil supply system configured to supply an oil that is used for both of lubrication of the reduction gear unit and cooling of the motor unit; and the diagnostic device as claimed in claim 1, wherein the motor unit comprises a plurality of motor units and the wheel comprises a plurality of wheels, one of the plurality of motor units being provided for each of the wheels, respectively.

9. The electric vehicle as claimed in claim 8, wherein the motor unit, together with a wheel bearing unit and the reduction gear unit, forms an in-wheel motor drive apparatus that is partly or entirely disposed within the wheel.

10. The electric vehicle as claimed in claim 9, wherein the reduction gear unit is in the form of a cycloidal gear device.

11. An electric vehicle configured to be able to be driven by the motor unit recited in claim 1.

12. The diagnostic device for the motor unit of the electric vehicle as claimed in claim 1, wherein the oil detection unit is further configured to detect an oil amount of the oil during the non-traveling period.

13. A diagnostic method for a motor unit of an electric vehicle including the motor unit configured to drive a wheel; a reduction gear unit configured to produce rotation with a speed that is reduced with respect to that of rotation of the motor unit; and an oil supply system having a pump configured to supply an oil that is used for both of lubrication of the reduction gear unit and cooling of the motor unit, the diagnostic method comprising:

detecting at least any one detection item of a contamination degree and a degradation degree of the oil by an oil detection unit only during a non-traveling period, the non-traveling period including a time of start-up and a time of stopping traveling, when the vehicle is powered on but power is not supplied to the motor unit from a control unit and the motor unit and the pump are not rotating;

configuring a motor drive controller to receive a motor torque command from the control unit or obtain a value of motor current that flows from an inverter to the motor unit using a current sensor;

configuring an abnormalities-time control unit, directly coupled to the motor drive controller, to send notice of abnormalities of the oil supply system and not permitting start of rotation of the motor unit when a detection value detected in the detection step is out of a setting range; and upon receiving the signal of abnormalities, limiting the motor torque command or the motor current produced from the inverter by the motor drive controller, whereby start of rotation of the motor unit is not permitted.

14. The diagnostic method for the motor unit of the electric vehicle as claimed in claim 13, further comprising detecting an oil amount of the oil during the non-traveling period.

* * * * *